(12) United States Patent
Nicholls et al.

(10) Patent No.: US 9,078,604 B2
(45) Date of Patent: Jul. 14, 2015

(54) LANCING DEVICES

(75) Inventors: Clive Nicholls, Aylesbury (GB); Robert Michael Wozencroft, Epsom (GB)

(73) Assignee: OWEN MUMFORD LIMITED, Oxford (GB)

(*) Notice: Subject to any disclaimer, the term of this patent is extended or adjusted under 35 U.S.C. 154(b) by 586 days.

(21) Appl. No.: 12/673,645

(22) PCT Filed: Aug. 14, 2008

(86) PCT No.: PCT/GB2008/002746
§ 371 (c)(1),
(2), (4) Date: Apr. 22, 2010

(87) PCT Pub. No.: WO2009/022136
PCT Pub. Date: Feb. 19, 2009

(65) Prior Publication Data
US 2011/0022070 A1 Jan. 27, 2011

(30) Foreign Application Priority Data
Aug. 14, 2007 (GB) .................................. 0715803.3

(51) Int. Cl.
*A61B 5/15* (2006.01)
*A61B 5/151* (2006.01)

(52) U.S. Cl.
CPC .......... *A61B 5/1411* (2013.01); *A61B 5/15186* (2013.01)

(58) Field of Classification Search
CPC .......... A61B 5/15186; A61B 5/15188; A61B 5/1519; A61B 5/1411

USPC .................................. 600/583; 606/181–186
See application file for complete search history.

(56) References Cited

U.S. PATENT DOCUMENTS

| 4,577,630 | A | 3/1986 | Nitzsche et al. |
| 6,042,595 | A | 3/2000 | Morita |
| 6,464,649 | B1 | 10/2002 | Duchon et al. |
| 2005/0234494 | A1 | 10/2005 | Conway et al. |
| 2006/0247670 | A1 | 11/2006 | LeVaughn et al. |

FOREIGN PATENT DOCUMENTS

| EP | 0 750 881 | 1/1997 |
| EP | 1 586 268 | 10/2005 |
| EP | 1 683 483 | 7/2006 |
| WO | 2006/067119 | 6/2006 |

OTHER PUBLICATIONS

International Search Report dated Nov. 24, 2008, from corresponding PCT application.
British Search Report dated Nov. 9, 2007, from corresponding priority application.

*Primary Examiner* — Ashley Fishback
(74) *Attorney, Agent, or Firm* — Young & Thompson (57) ABSTRACT

A lancing device includes a main barrel portion 10 to the front end of which is hinged a forward portion for movement between the open position shown in FIG. 1 and a closed position. The main barrel portion 10 contains a drive mechanism, cocking slider and trigger, while the forward portion contains a lancet holder into which a lancet may be loaded front end first. Also disclosed is a lancing device having a main housing having a forward nose portion to the rear of which is a flip up lancet hatch into which a lancet may be loaded front end first.

20 Claims, 15 Drawing Sheets

LANCING DEVICES

This invention relates to lancing devices and in particular, but not exclusively, to lancing devices for use with a removable lancet.

There are many instances where a user needs to prick the skin to draw a bead of blood for test purposes. To reduce the possibility of cross infection or contamination, it is known to provide a lancing device with a disposable lancet, which is removed and disposed of after each use. In existing such devices it is common for the lancet to be inserted into the lancing device rear end first to leave the forward end of the lancet (including the lancet needle or tip) facing forwardly. Although in many cases the lancet tip is initially shrouded to keep it sterile and to protect the user (for example with a moulded on, twist off cap), there is a risk that this cap may be dislodged prematurely leaving the tip exposed, thus causing injury when pressing the lancet home to load it into the lancing device, or that the lancet tip may be bent.

In this specification, the terms "forward" "rearward" etc refer to the device when in a closed position, with the forward end being that from which the lancet momentarily projects. U.S. Pat. No. 6,464,649 discloses a device in which a separate tip assembly is screwed onto the front end of a sample device and receives a replaceable tip. The screwing action is cumbersome and awkward for those of impaired dexterity, and handling of the three separate components is inconvenient.

In one aspect, this invention provides a lancing device for use with a removable lancet, and having a drive for causing a lancet to be fired momentarily to project from the device to prick a user's skin, said device comprising a main housing and a captive pivotally mounted mousing portion configured to be openable to allow insertion of a removable lancet front end first into a guide or holder and then to be closed ready for firing.

In this manner, the insertion force to push the lancet into the guide or holder is on the rear end.

In another aspect, this invention provides a lancing device for use with a removable lancet and having a drive for causing a lancet to be fired momentarily to project from said housing to prick the skin of the user, said housing comprising a main portion containing said drive and a captive movable forward portion pivotally coupled to said main portion and movable between a closed, firing position and an open loading/unloading position in which a lancet holder is accessible to allow insertion of a removable lancet front end first.

Preferably, said lancet holder is mounted for longitudinal movement within said forward portion.

In order to minimise the possibility of injury during loading, stop means is preferably provided to restrict forward movement of said lancet holder when said forward portion is in its open position.

Preferably said stop means includes an arm extending from said main body portion and adapted to block or restrict movement of said lancet holder forwardly with respect to said forward portion when the latter is open. Conveniently, two such arms may be provided, which engage one to each side of said lancet holder.

Conveniently, there may be means biasing said forward portion towards an open position. Advantageously, the device may include releasable latch means for latching said movable portion in the closed position. Damping means may be provided for damping said opening movement.

Whilst the invention has been described above it extends to any inventive combination or sub-combination of the features set out above or in the following description.

The invention may be performed in various ways, and two embodiments thereof will now be described by way of example only, reference being made to the accompanying drawings, in which:—

Figure 1:
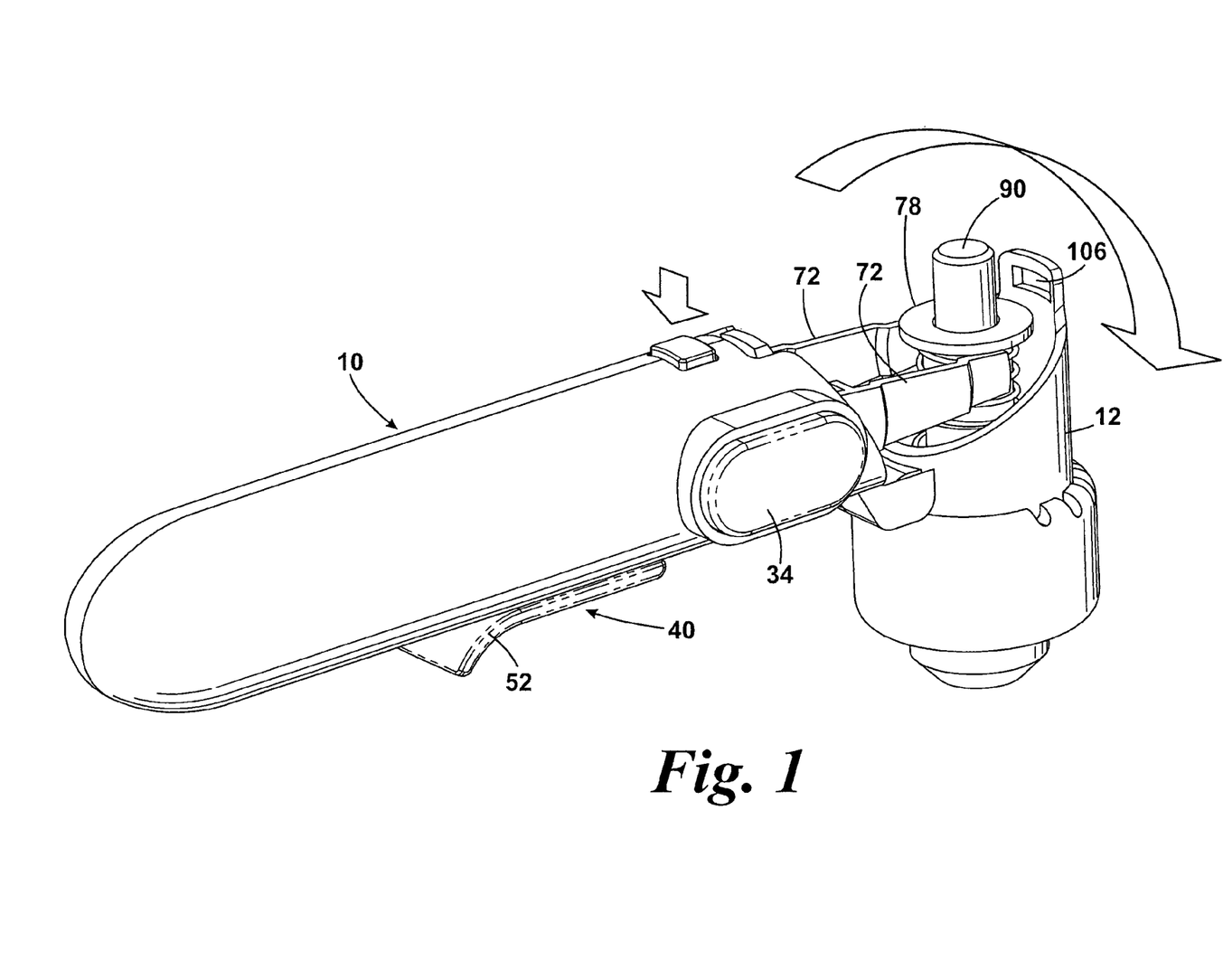
FIG. 1 is a general perspective view of a first embodiment of lancing device in accordance with this invention in a loading/unloading configuration.
Figure 2:
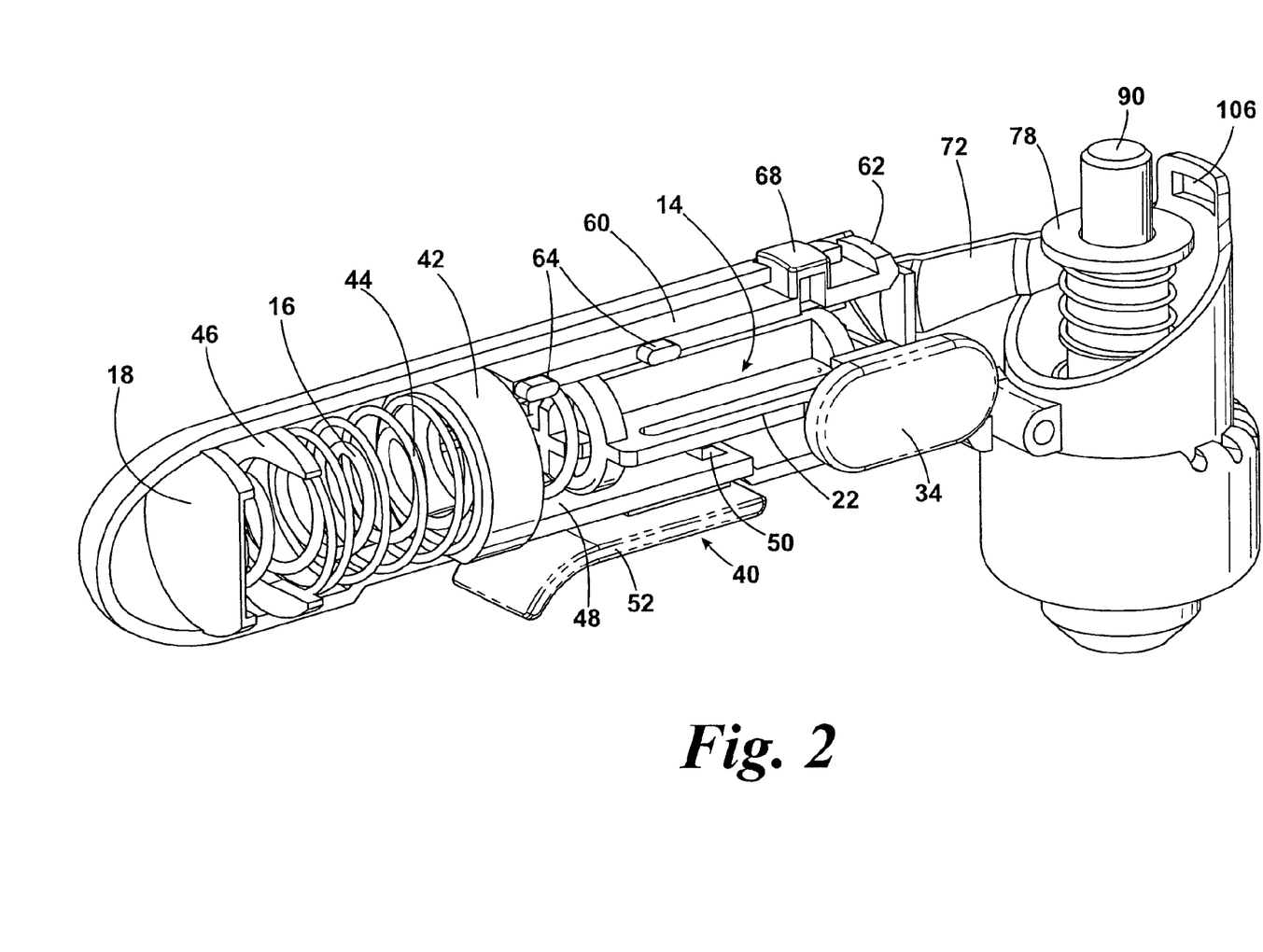
FIG. 2 is a view similar to FIG. 1 but showing part of the main barrel removed.
Figure 3:
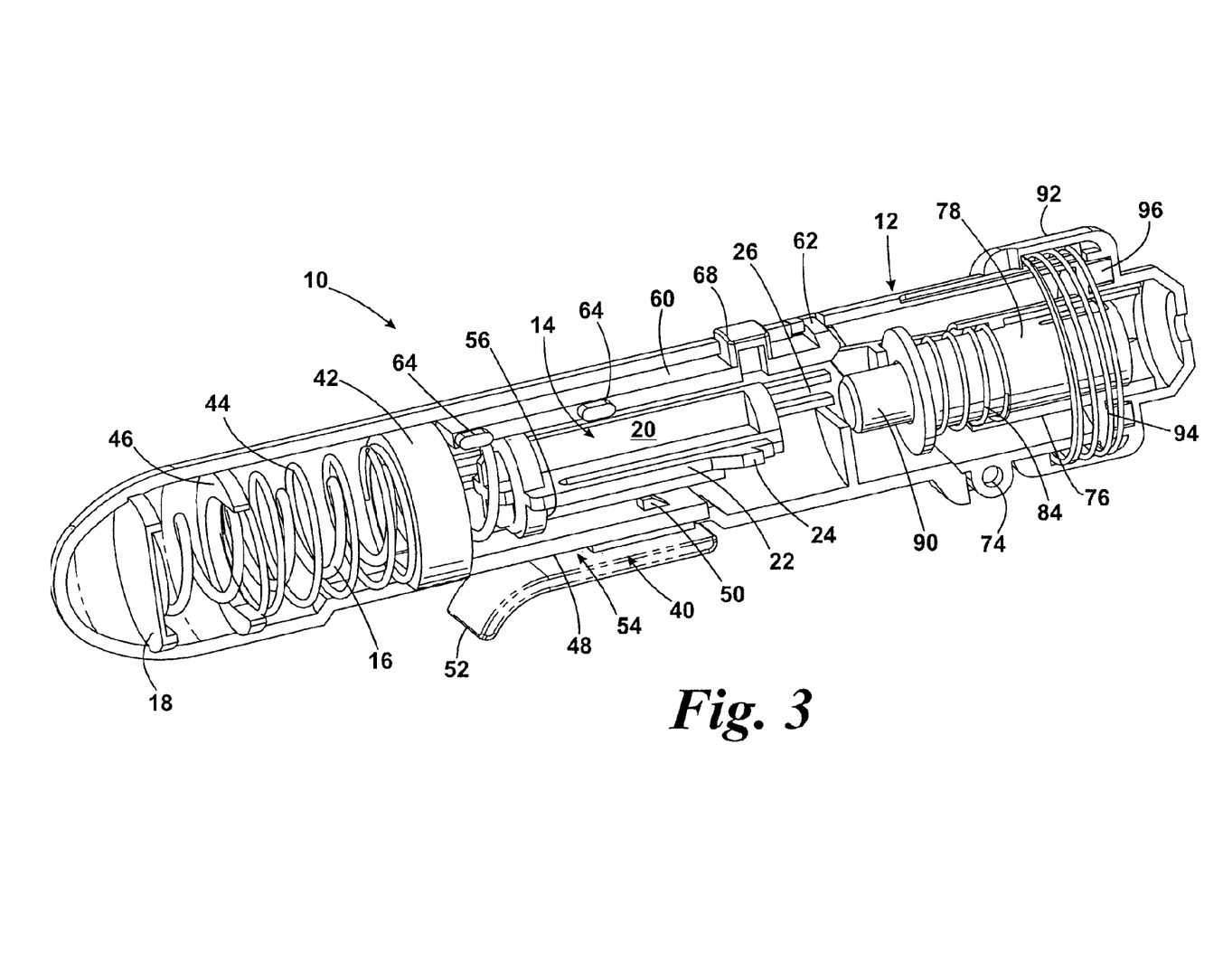
FIG. 3 is a view similar to FIG. 2 but showing the device in its closed, firing position.
Figure 4:
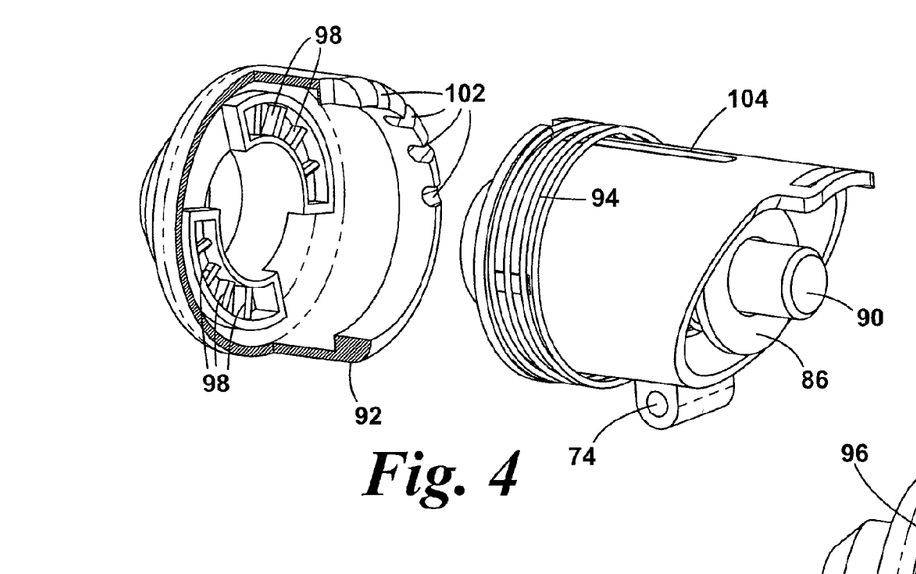
FIG. 4 is an exploded, detailed view on the front end of the device showing the depth adjuster.
Figure 5:
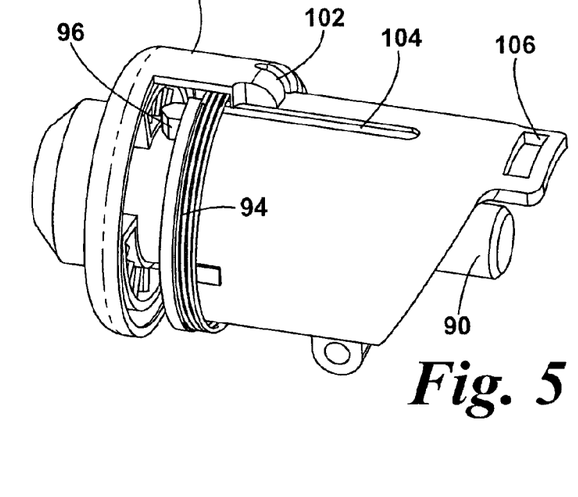
FIG. 5 is a view similar to FIG. 4 but showing the components when assembled.
Figures 6A, 6B:
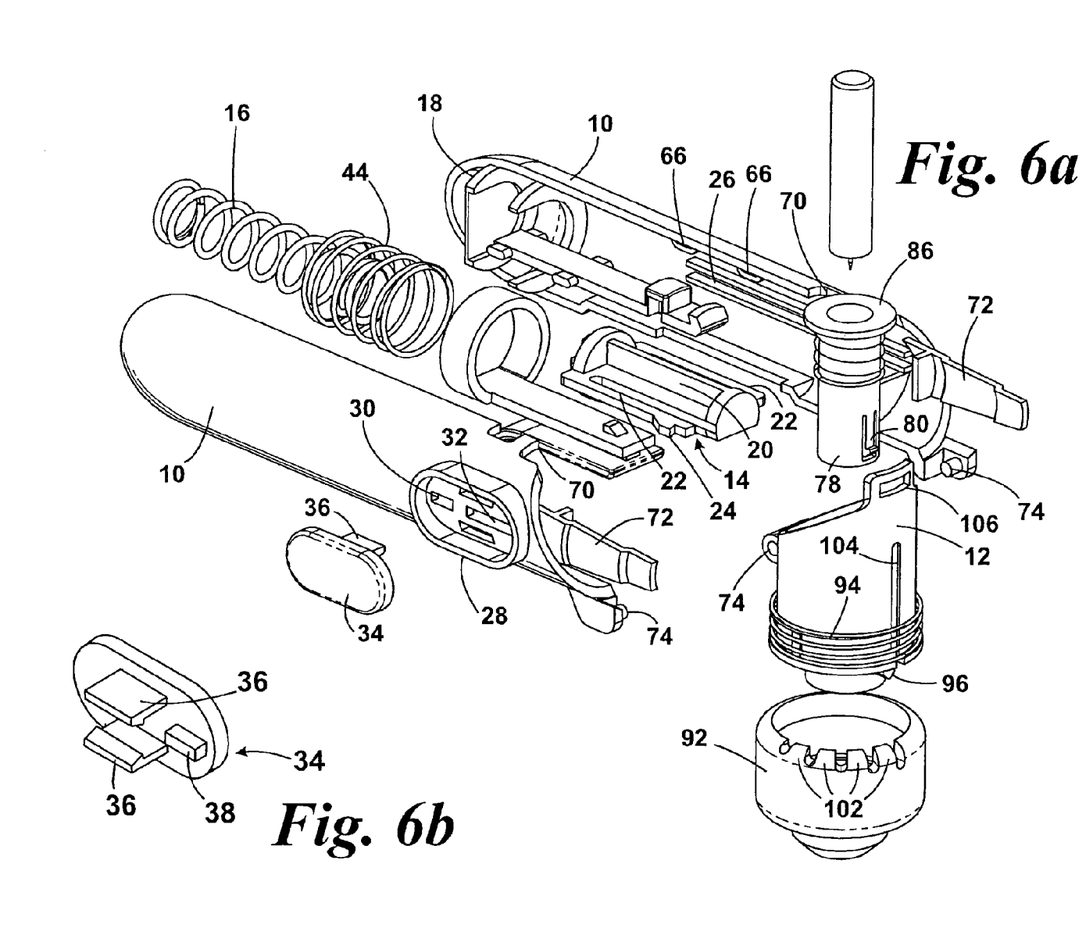
FIG. 6(a) is an exploded view showing the lancing device in its loading/unloading configuration and FIG. 6(b) is a detailed view on the trigger button.
Figure 7:
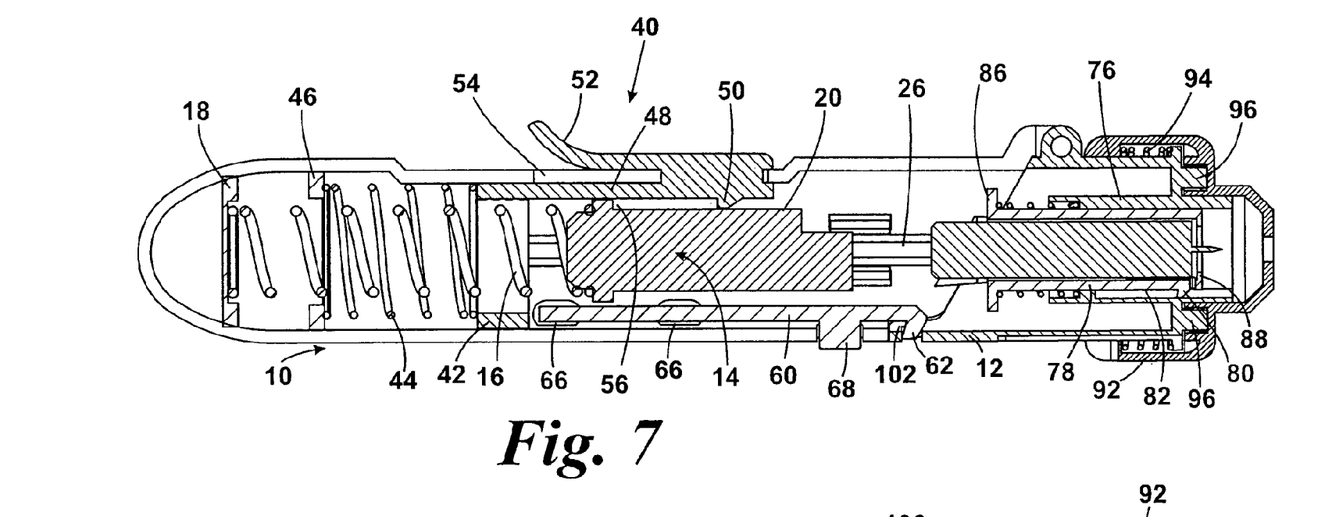
FIG. 7 is a side section view of the device when closed.
Figure 8:
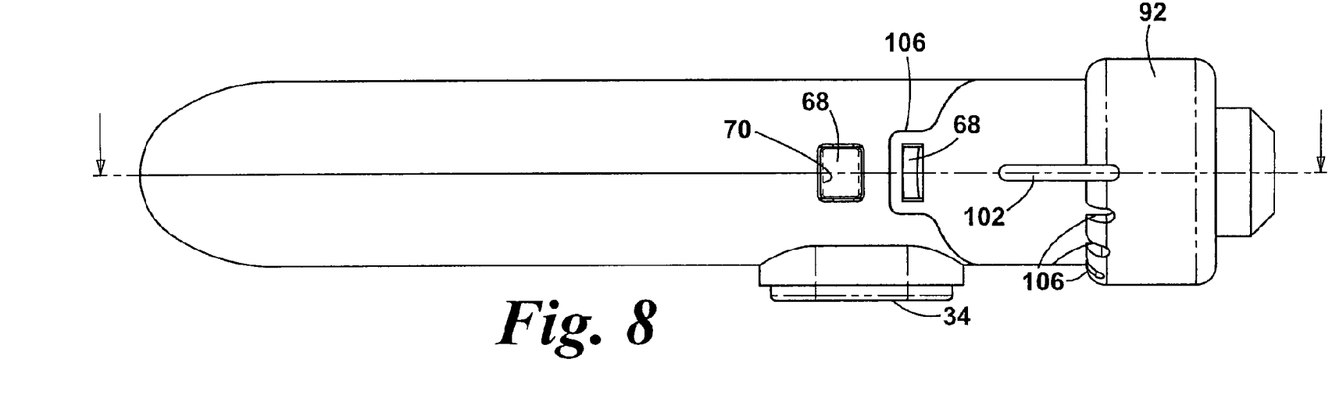
FIG. 8 is a top plan view of the first embodiment.

Referring initially to the FIGS. 1 to 7, the first embodiment of lancing device disclosed therein has a main barrel portion 10 to the front end of which is hinged a forward portion 12 for movement between the open position shown in FIGS. 1 and 2, and the closed position shown in FIGS. 3, 7 and 8. The main barrel portion 10 contains the drive mechanism, cocking slider and trigger, whilst the forward portion 12 contains a lancet holder and the lancet as to be described below.

Within the main barrel portion 10 is slidably mounted a hammer 14 urged forwardly by a drive spring 16 which is seated at its rear end on an internal wall 18 of the main barrel portion 10. The hammer 14 has a main body portion 20 and two integral arms 22, one of which carries a barbed portion 24. The arms 22 are received in respective U-shaped guides 26 formed in diametrically opposed regions of the internal wall of the main barrel portion. The right hand side of the main barrel 10 includes an integrally formed trigger housing 28 in the base of which, communicating with the V guide 26, are a cocked slot 30 and a forward drive slot 32 (see FIG. 9).

When the hammer 14 is cocked, as to be described below, the barbed portion 24 of the resilient arm 22 latches into the cocked slot 30 to hold the hammer in the cocked position. A trigger button 34 is held captive in the slot by two barbed arms 36 and includes a trigger finger 38 aligned with the cocking slot 30. With the hammer 14 cocked, pressing the trigger button 34 causes the trigger finger 38 to project into the cocking slot 30 to release the barbed portion 24 so that the hammer may move forwardly under the influence of the drive spring 16. As the hammer moves forwardly, the arm 22 with the barb on it flexes outwardly so that the barb enters the forward drive slot 32 and the hammer comes to a rest when the barbed portion 24 hits the forward end of the forward drive slot 32 after it has impacted the rear of the lancet. A cocking slide 40 comprises a rear sleeve 42 urged forwardly by a return spring 44 acting at its rear end of an inner wall 46 of the main barrel portion 10. Extending forwardly of the rear sleeve 42 is a rectangular strip 48 having an inwardly directed barb 50. Joined to the underside of the strip 48, is a thumb piece 52 which projects externally through a slot 54 in the main barrel portion.

When the hammer 14 has been fired, and is in its forwardmost position, the cocking slide 40 may be pulled rearwardly such that the barb 50 engages an abutment surface 56 on the rear end of the trigger to pull it back to the cocked position with the barbed portion 24 on the hammer arm 22 engaging the cocking slot 30 to retain the hammer in the cocked position ready to be released by pressing the trigger button 34.

Figure 9:
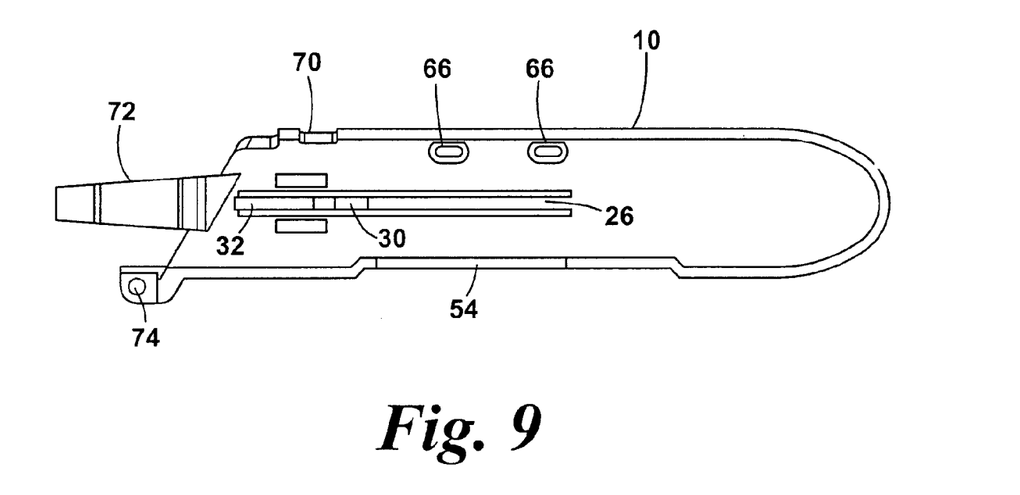
FIG. 9 is a detailed view on one half of the main barrel portion.
Figure 10:
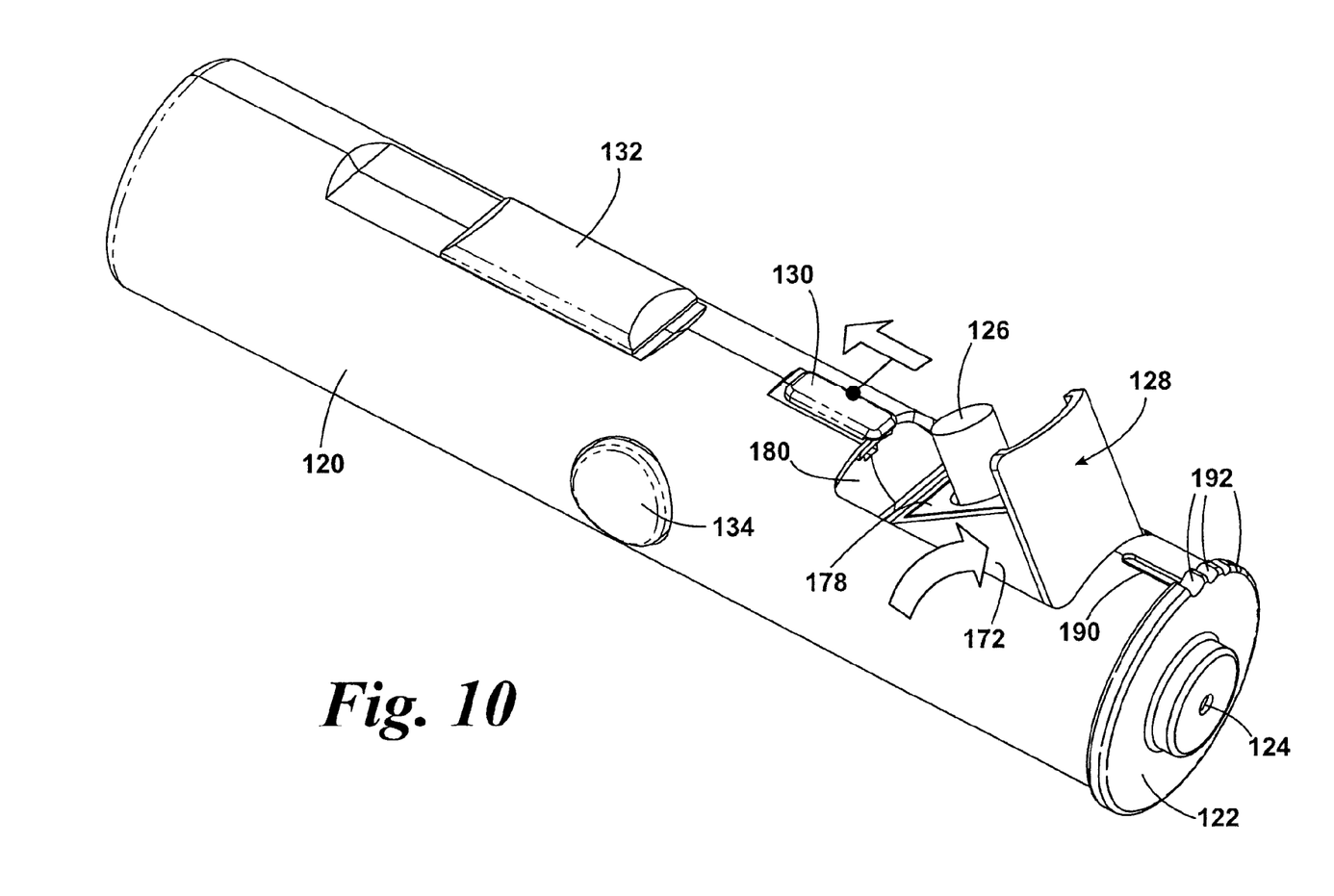
FIG. 10 is a general perspective view of a second embodiment of lancing device in accordance with this invention with the hatch open.

Mounted in the casing on the opposite side from the cocking slide 40 is a flexible latch comprising a main body 60, a latching portion 62, the latch being anchored in the housing by lugs 64 received in moulded recesses 66 in the housing (see FIG. 9). A latching button 68 projects through an aperture 70 in the main barrel.

Extending forwardly of the main barrel portion are two arms 72 for the purposes to be described in more detail below. The hinged forward portion 12 is hinged at 74 to the main body portion 10. The forward portion 12 supports an inner concentric sleeve 76 (FIGS. 3 and 7) within which is mounted for sliding movement a lancet holder 78. The lancet holder has a sprung tooth 80 that slides in a blind key way 82 in the inner sleeve 76 to limit rearward movement of the lancet holder. A spring 84 acts between an outer flange 86 on the lancet holder 78 and the inner sleeve 76. The spring 84 is shown in the equilibrium position in FIG. 7 and then compresses from the equilibrium position when the lancet is fired.

The lancet holder 78 has a forwardly inturned flange 88 for engaging the front end of the lancet. The outwardly directed flange 86 is designed to cooperate with the forward arms 72 on the main barrel portion so that, when the housing is hinged forwardly, the ends of the arms 72 engage in front of the flange 86 and pull it slightly rearwardly relative to the forward housing and also prevent forward movement thereof when the lancet is loaded into the holder.

A rotatable nose piece 92 is captively mounted on the forward end of the forward portion 12, and urged rearwardly relative to the housing by a compression spring 94. As seen more clearly in FIGS. 5 and 6, the forward end of the forward housing is provided with two diametrically opposed forwardly facing V projections 96. These cooperate with respective abutments 98 of different axial extent, separated by dividing walls 100. This arrangement allows the axial position of the nose piece 92 relative to the forward portion 12 to be adjusted by pulling the nose piece 92 forwardly against the spring bias, turning it to the required position and releasing it so that axial position is determined by the thickness of the abutment 98. The nose piece 92 includes notches 102 indicative of the axial position, and a marker slot 104 is provided on the forward portion 12. The meeting faces of the main barrel portion 10 and the forward portion are at an acute plane relative to the longitudinal axis of the device, and a catch portion 106 on the forward portion 12 of the housing cooperates with the latching portion 62.

In use, the device is opened by depressing the latching button 68, and hinging the portion 12 forwardly to "break" the device. In doing this, the arms 72 cooperate with the flange 86 on the lancet holder 78 to pull it slightly rearwards relative to the portion 12 and to hold it against forward movement. An existing lancet 90 can be pulled out and replaced by a new lancet which is inserted front end first into the device. The arms 72 preventing movement of the lancet holder remove the possibility of the lancet being pushed forwardly through the aperture of the nose piece. The front portion 12 is then snapped shut. The cocking slide 40 is then drawn rearwardly to pull the hammer 20 against the drive spring 16 back to its cocked position with the barb 24 seating in cocking slot 30. The user then may select the appropriate penetration depth by pulling, twisting and releasing the nose piece 12. Once armed in this way, the user offers the device up to their skin and presses the trigger button 34. The hammer 14 shoots forward to impact the rear of the lancet 90, driving it momentarily to project from the nose piece and puncture the skin. Thereafter the hammer and lancet adopt the equilibrium position shown in FIG. 7.

Referring now to the second embodiment illustrated in FIGS. 10 to 17, the lancing device comprises a housing made of two main housing halves 120 of generally semi-cylindrical form, at the front end of which is provided a nose portion 122 having an aperture 124 through which the tip of a lancet (not visible in FIG. 10) protrudes when fired. Just to the rear of the nose portion 122 is a flip-up lancet hatch 128 to and from which the lancet may be loaded and unloaded. The flip-up hatch is released by a release button 130. The lancet is cocked by a slider 132 and, once cocked, the lancet is fired by pressing the trigger button 134.

Internally of the housing 120 there is slideably mounted a hammer 136 which is constrained for longitudinal movement by means of lateral ribs 138 which run in opposed channels 140 on the interior walls of the housing halves. The hammer is urged forwardly by a drive spring 142 located between the rear end of the hammer 136 and the inner surface of the end wall 144 of the main housing. Forward movement of the hammer 136 is limited by a stop surface 146 connected to the main housing. Upstanding from the rear end of the hammer 136 is a cocking abutment 148 which cooperates with a complementary abutment 150 protecting inwardly from the cocking slider 132. The cocking slider has an externally accessible portion and an inner spring support ring 152 which is urged forwardly by a compression spring 154 acting on an interior wall 156 in the housing.

The left hand main housing half 120 (when viewed from the front) has the trigger button 134 captively mounted therein for inward movement. The trigger button 134 is retained by barbed legs 158 engaged in recesses 160 in the housing wall. Between the barbed legs 158 is a shorter trigger finger 162 which cooperates with a latching recess 164 disposed in the groove 140. The lateral rib 138 of the hammer 136 engaging the associated groove 140 is formed with a resiliently flexible portion carrying a barb 166 that locates in the latching recess 164 when the hammer is pulled rearwardly, to latch it in a cocked position. Pressing the trigger button 134 pushes the barb 166 out of the latch recess 164 so that the hammer is driven forwardly by the drive spring 142.

The lancet hatch 128 comprises an upper arcuate panel 170 which, when the hatch is in its closed position, conforms to the surrounding cylindrical surface of the main housing. The hatch 128 is rotatably mounted in the forward end of the device by means of hinge lugs 170 extending to either side of a box portion 172 of the hatch. A torsion spring 174 urges the hatch to its open position. Suitable damping provision may be included to produce damping for the opening movement. Within the box portion 172 is mounted a lancet holder 176 which is urged rearwardly by a compression spring 178 but held captive to the box portion by a tooth 179. The lancet holder 176 includes an inwardly directed rib 181 at its inner end to limit forward movement of a lancet 126 when inserted.

Figure 11:
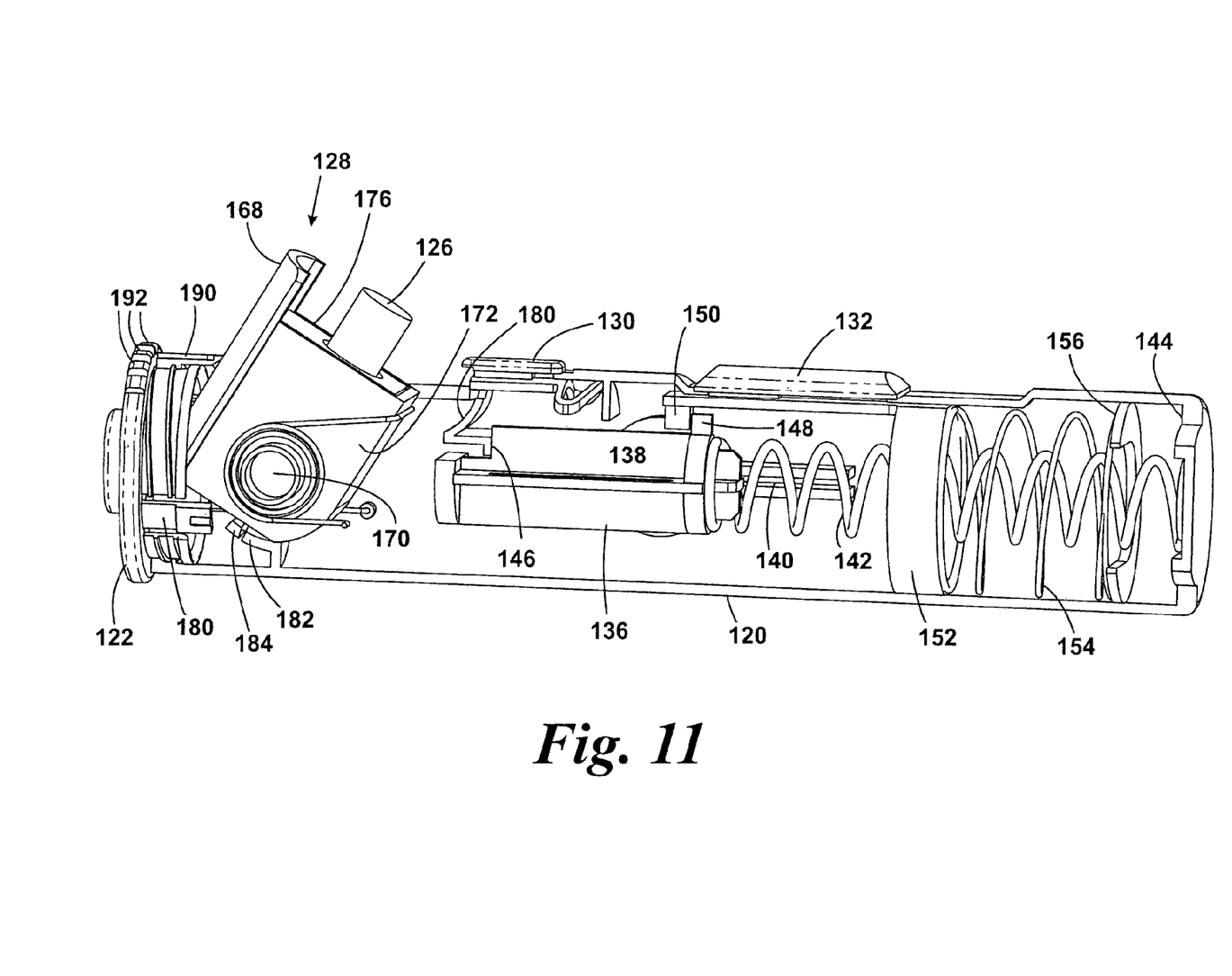
FIG. 11 is a side view with part of the barrel removed of the second embodiment of lancing device with the hatch open.
Figure 14:
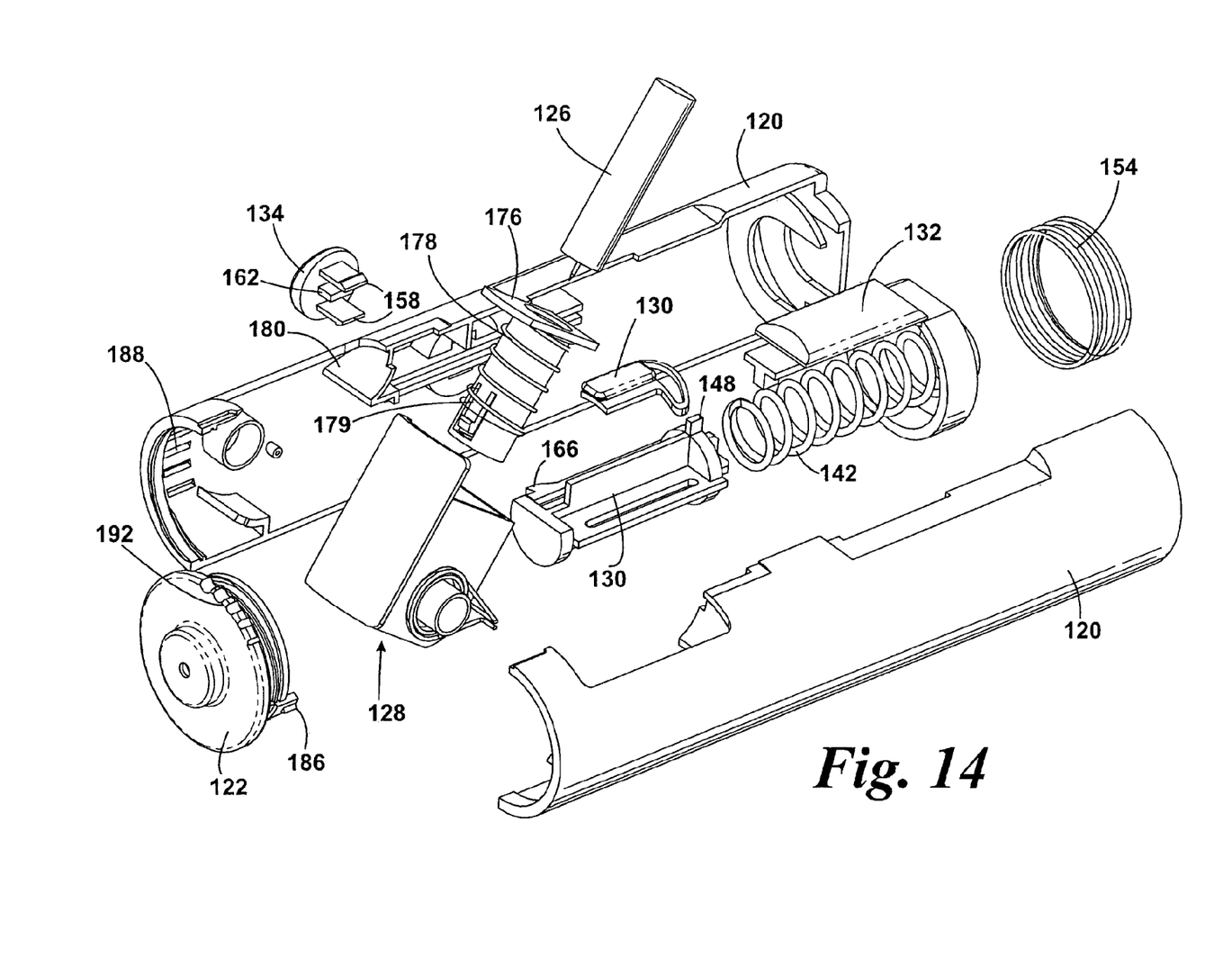
FIG. 14 is an exploded view of the second embodiment of lancing device.
Figure 15:
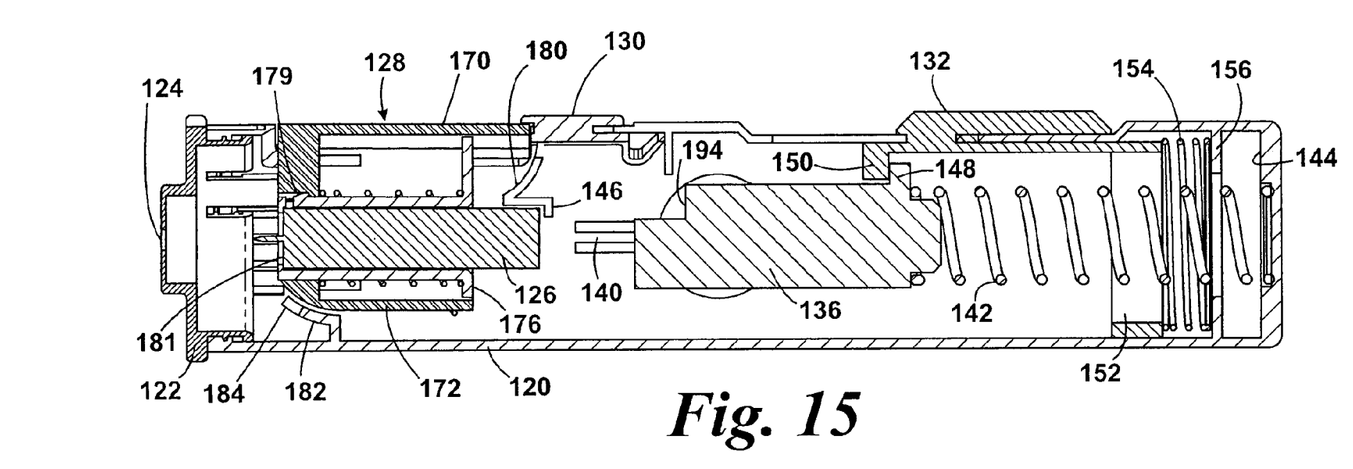
FIG. 15 is a longitudinal section view through the second embodiment with the hatch closed and the hammer cocked.
Figure 16:
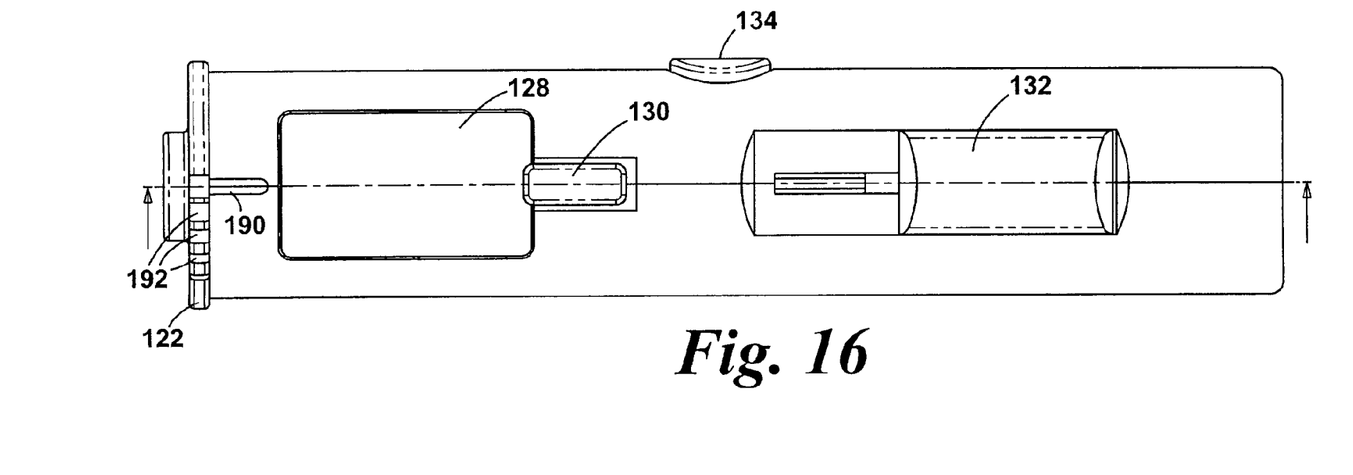
FIG. 16 is a top plan view of the second embodiment.
Figure 17:
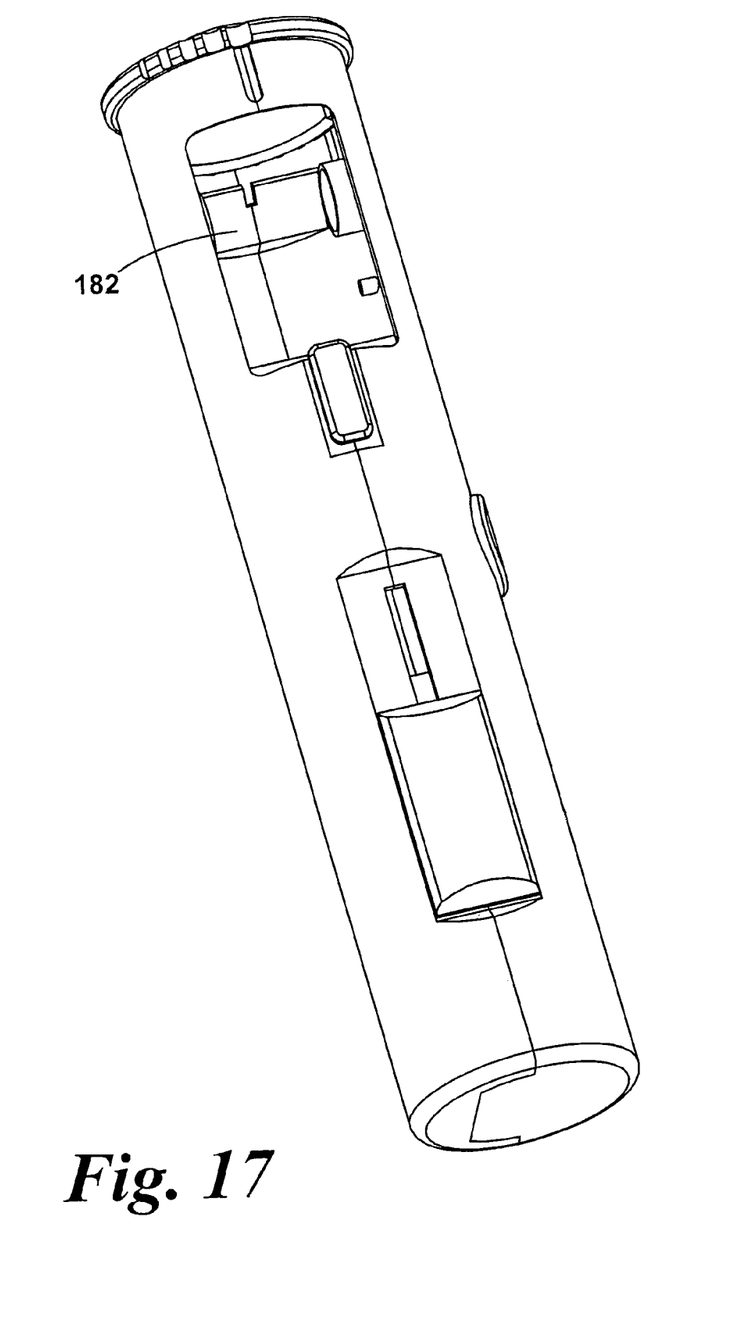
FIG. 17 is a view on the interior of the housing, showing the arcuate lancet restraint.
Figure 18:
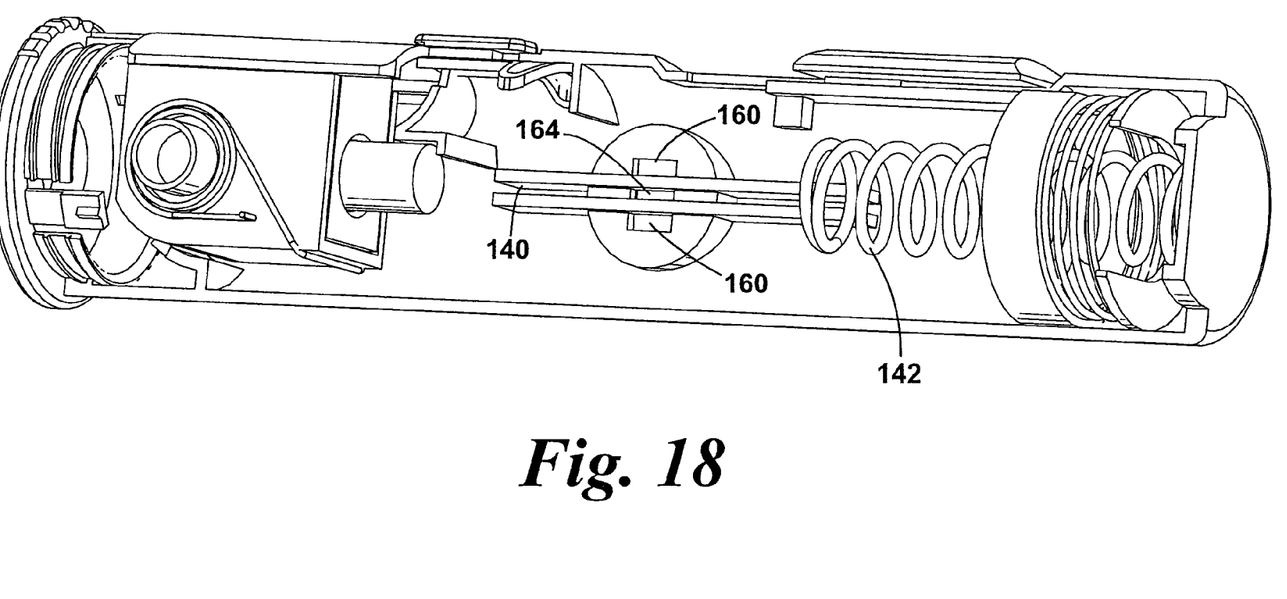
FIG. 18 is a view of the latch recess and trigger mounting on one of the housing halves of the second embodiment.
Figure 19:
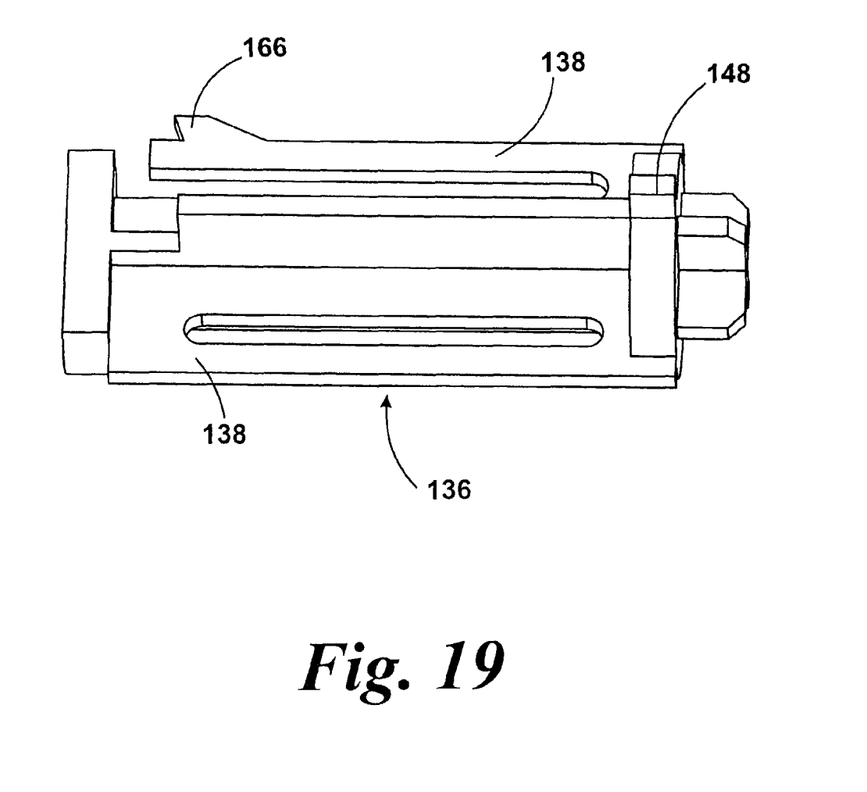
FIG. 19 is a perspective view of the hammer of the second embodiment.

When the lancet holder is in its open position as shown in FIGS. 11 and 14, the compression spring 178 is free to urge the lancet holder back to its rearmost position, flush with the end of the box portion 172. Adjacent the arc of movement of the rear end of a lancet 126 when inserted into the holder is a latch surface 180 which is part of the same formation as the stop surface 146 forming part of the inner wall of the housing. The function of the latch surface 180 is to engage the end of a lancet 126 to urge it forwardly to lightly compress the spring 178 until the hatch is closed with the lancet 126 aligned with the hammer 136, and as described below later to latch the hatch closed when the hammer is cocked.

In the forward lower part of the housing is an arcuate support surface 182 designed to cooperate with the forward face of the lancet 126/lancet holder 176 to prevent forward movement as the lancet is being loaded. The arcuate surface is provided with a notch 184 to receive the lancet tip.

The nose portion 122 is threadedly engaged for the corresponding threaded portion in the inner surface of the front end of the main housing 120 such that the penetration depth of the lancet can be adjusted by twisting the nose piece to move it axially in and out. The nose piece has diametrically opposed arms 186 which engages detents 188 in the inner surface of the housing to provide a click setting. A marker groove 190 is provided on the housing and different sized notches 192 on the end of the cap indicate the depth set.

Figure 12:
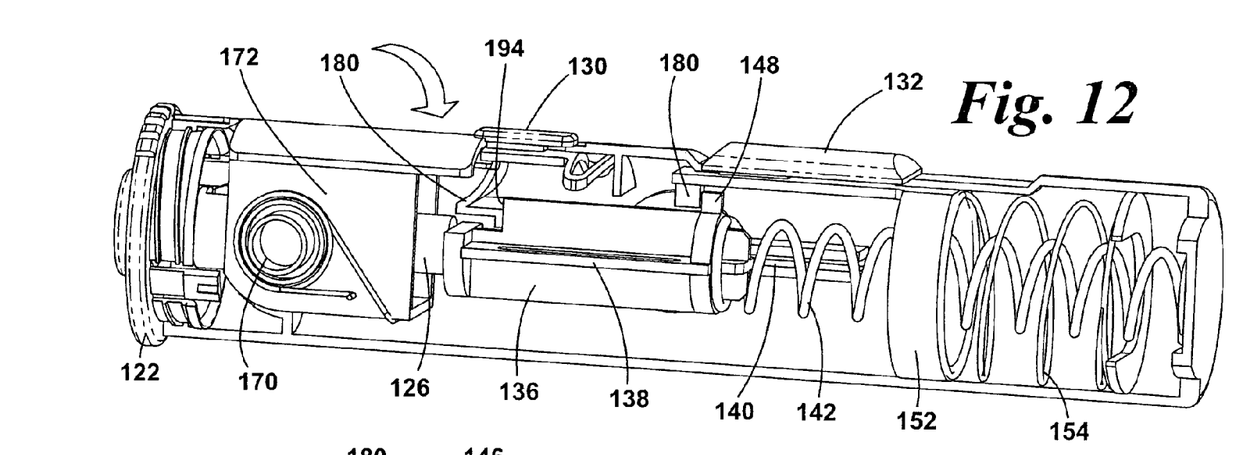
FIGS. 12 and 13 are views similar to FIG. 11 but showing shutting of the hatch following loading, and cocking the hammer of the device respectively.
Figure 13:
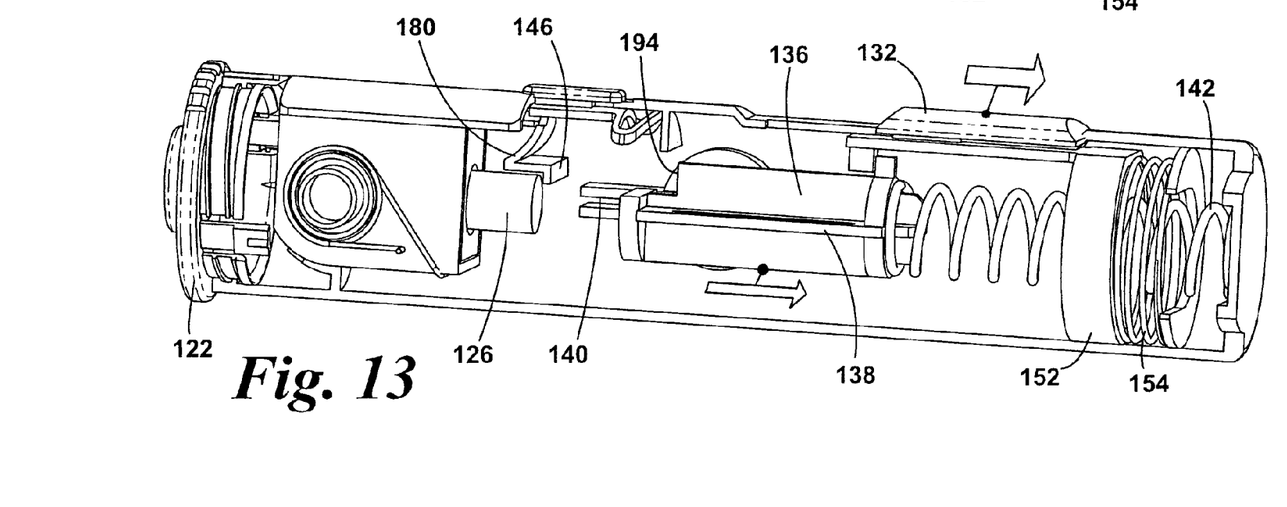

In use, the hatch 128 is opened by pulling back the release button 130 to flip the hatch open so that the previous lancet 126 is presented for removal. The lancet is removed and replaced by a new lancet and the hatch snapped shut (FIG. 12). The hammer 136 is still uncocked, and at its forwardmost position, with a forward ledge 194 abutting the stop surface 146. In this position, the front face of the hammer 136 is level with the forward apex of the ramp surface 180 and so the spring 178 is still lightly compressed, and the hatch may be reopened if necessary. From here, the cocking slider 132 is slid rearwardly, pulling the hammer back with it until the barb 166 latches in the latch recess 164. The cocking slider 132 is then released and allowed to return to its original position. During this process, as seen in FIG. 13, the lancet moves rearwardly under the influence of the spring 178, into its blocking position beneath the ramp 180, which prevents opening of the hatch (FIG. 13).

The user then offers the device up to their skin and presses the trigger button 134. The hammer is released, shooting forwards to impact upon the rear end of the lancet to cause it to momentarily project through the aperture 124 and prick the skin. The hammer is arrested by the ledge 194 contacting the stop surface 146 and, having shot forwards, the lancet then retracts into the housing under the influence of the spring 178 so the components adopt the position shown in FIG. 12. The hatch may be opened by releasing the release button 130.

It will be noted that in the second embodiment, the cap or platform is left in place during loading and unloading of the lancet. This means that there is minimal disturbance to the penetration setting.

The invention claimed is:

1. A lancing device for use with a removable lancet (90, 126) having a front end and a rear end and a pricking tip at its front end, said device comprising:

a drive (44, 142) for causing a lancet to be fired momentarily to project the tip forwardly from the device to prick the user's skin;

a main housing (10, 120) having a front end and a rear end, the main housing containing said drive;

a captive pivotally mounted housing portion (12, 128) mounted to the main housing for pivotal movement about an axis spaced forwardly of the rear end of the main housing, and a lancet guide or holder provided in said captive pivotally mounted housing portion, the lancet guide or holder defining a passage having a forward and a rearward end and being adapted to receive a lancet, such that in use, the lancet is located in the passage with the tip of the lancet facing towards the front end of the device, the pivotally mounted housing portion being at least one of
 i) disposed in a forward region of said main housing, and
 ii) disposed adjacent a forward end of the main housing, and the pivotally mounted housing portion being openable between i) an open position, which provides access to the rearward end of the lancet guide or holder passage to allow removal of a previous removable lancet and to allow insertion of a replacement removable lancet (90, 126) front end first into said lancet guide or holder passage (78, 176) with the tip of the lancet facing towards the forward end of the lancet guide or holder, and ii) a closed position, in which the device is ready for firing.

2. A lancing device for use with a removable lancet (90, 120) having a front end and a rear end and a pricking tip at its front end, said device comprising:

a housing; and a drive (44, 142) for causing a lancet to be fired momentarily to project the tip forwardly from the housing to prick the skin of a user, said housing comprising a) a main portion (10, 120) containing said drive (44, 142), the main portion having a front end and a rear end, b) a captive movable forward housing portion (12, 128) pivotally coupled to said main portion (10, 120) for pivotal movement about an axis spaced forwardly of the rear end of the main portion, and c) a lancet guide or holder provided in said pivotally mounted forward housing portion (12, 128), the lancet guide or holder defining a passage having a forward and a rearward end, such that in use, the lancet is located in the passage with the tip of the lancet facing the front end of the device, the pivotally mounted forward housing portion (12, 128) being at least one of
i) disposed in a forward region of said main portion, and
ii) disposed adjacent a forward end of the main portion, the pivotally mounted forward housing portion being movable between a closed, firing position and an open loading/unloading position which provides access to the rearward end of the lancet guide or holder passage to allow removal of a previous removable lancet and to allow insertion of a replacement removable lancet front end first into said lancet guide or holder passage (78, 176) with the tip of the lancet facing towards the forward end of the lancet guide or holder.

3. The lancing device according to claim 2, wherein said lancet holder (78, 176) is mounted on said forward housing portion (12, 128) for longitudinal movement with respect thereto.

4. The lancing device according to claim 3, wherein a stop element (72, 182) is provided to restrict forward movement of said at least one of said lancet (90, 126) and lancet holder (78, 176) when said pivotally mounted forward housing portion is in its open position.

5. The lancing device according to claim 4, wherein said stop element (72) includes an arm extending from said main portion (10) and adapted to block movement of said lancet holder (78) when said forward housing portion is open.

6. The lancing device according to claim 2, including a biasing element (174) biasing said forward housing portion towards an open position.

7. The lancing device according to claim 2, which includes a damping element for damping said opening movement.

8. The lancing device according to claim 2, which includes a releasable latch releasably latching said movable forward housing portion in the closed position.

9. The lancing device according to claim 2, including a damper element for damping said spring movement.

10. The lancing device according to claim 2, wherein said forward housing portion (10) has a forward face for engaging the skin of a patient in use.

11. The lancing device according to claim 2, wherein the main portion (120) has a forward face portion (122) for engaging the skin of a patient in use.

12. The lancing device according to claim 11, wherein said pivotally mounted forward housing portion comprises a hatch (128) disposed rearwardly of said forward face portion (122), said hatch including said lancet holder guide or holder being pivotable between a first position in which the guide or holder (176) is operationally aligned with said drive and a loading/unloading position in which the guide or holder is rearwardly accessible to receive a lancet.

13. The lancing device to according to claim 12, which includes a support surface (182) disposed adjacent said hatch (128) so that, when the hatch is in its open position, said surface limits forward movement of said lancet.

14. The lancing device according to claim 13, wherein said support surface (182) includes a cut away region (184) to receive the lancet tip.

15. The lancing device according to claim 12, wherein the lancet holder (176) is slideably mounted in said hatch portion (128) and biased rearwardly by a spring element (178).

16. The lancing device according to claim 15, including a ramp element (180) disposed adjacent the arc of movement of the hatch (128) and disposed to cooperate with the lancet (128) or lancet holder (176) so that, as the hatch is closed, said spring element is compressed (178).

17. The lancing device according to claim 16, wherein said drive element comprises a hammer (136) moveable against a spring bias (142) from a forward position to a rearward cocked position, and arranged relative to said ramp element such that, when said hammer (136) is in its forward position, on closing said hatch (128) said lancet (126) is brought into contact with the front end of said hammer (136) with residual compression in said spring element.

18. The lancing device according to claim 17, wherein a stop surface (146) is provided adjacent or contiguous with said ramp element (180), said stop surface being arranged such that, on rearward movement of said hammer (136) for cocking, the lancet (126) moves rearwardly to cooperate with said stop surface to block opening of said hatch.

19. The lancing device according to claim 2, wherein the pivotally mounted forward housing portion (12, 128) is disposed in a forward region of said main portion housing.

20. The lancing device according to claim 2, wherein the pivotally mounted forward housing portion (12, 128) is disposed adjacent a forward end of the main portion.

* * * * *